(12) United States Patent
Yuuki et al.

(10) Patent No.: US 7,329,521 B2
(45) Date of Patent: Feb. 12, 2008

(54) TRANSGLUTAMINASE-PRODUCING STRAIN

(75) Inventors: Kensuke Yuuki, Kakamigahara (JP); Kinya Washizu, Kakamigahara (JP)

(73) Assignee: Amano Enzyme Inc., Nagoya-Shi (JP)

( * ) Notice: Subject to any disclaimer, the term of this patent is extended or adjusted under 35 U.S.C. 154(b) by 0 days.

(21) Appl. No.: 10/527,090

(22) PCT Filed: Sep. 9, 2003

(86) PCT No.: PCT/JP03/11473

§ 371 (c)(1), (2), (4) Date: Mar. 10, 2005

(87) PCT Pub. No.: WO2004/024912

PCT Pub. Date: Mar. 25, 2004

(65) Prior Publication Data

US 2006/0035366 A1    Feb. 16, 2006

(30) Foreign Application Priority Data

Sep. 10, 2002 (JP) ............................. 2002-263834

(51) Int. Cl.
*C12N 1/20* (2006.01)
*C12N 9/00* (2006.01)
*C12N 9/10* (2006.01)
*C12N 15/70* (2006.01)
*C12P 21/06* (2006.01)
*C12Q 1/68* (2006.01)
*C07H 21/04* (2006.01)

(52) U.S. Cl. ............... 435/193; 435/252.3; 435/252.35; 435/183; 435/6; 435/69.1; 435/320.1; 536/23.2

(58) Field of Classification Search ............. 435/252.3, 435/22.3, 183
See application file for complete search history.

(56) References Cited

U.S. PATENT DOCUMENTS

| | | | |
|---|---|---|---|
| 5,156,956 A | 10/1992 | Motoki et al. | |
| 5,328,998 A | 7/1994 | Labes et al. | |
| 5,420,025 A | 5/1995 | Takagi et al. | |
| 2002/0187525 A1 | 12/2002 | Taguchi et al. | |

FOREIGN PATENT DOCUMENTS

| | | |
|---|---|---|
| EP | 0 379606 B1 | 8/1990 |
| EP | 0 481504 B1 | 4/1992 |
| EP | 0 531717 A2 | 3/1993 |
| EP | 1219713 | 7/2002 |
| EP | 1225217 | 7/2002 |
| JP | 64-27471 | 1/1989 |
| JP | 5-199883 | 8/1993 |
| JP | 2001-186884 | 7/2001 |
| WO | WO 01/29187 A1 | 4/2001 |

OTHER PUBLICATIONS

Pulido et al. Optimization of gene expression in *Streptomyces lividans* by a transcription terminator. Nucleic Acids Res. May 26, 1987;15(10):4227-40.*
Trono et al. A human cell factor is essential for HIV-1 Rev action, EMBO J. Dec. 1990;9(12):4155-60.*
Supplementary European Search Report in corresponding application EP 03795322, dated Aug. 22, 2006.
J.M. Connellan, et al., "Structural Properties of Guinea Pig Liver Transglutaminase;" *The Journal of Biological Chemistry*; vol. 246; No. 4; Feb. 25, 1971; pp. 1093-1098.
J.E. Folk, et al.; "Molecular and Catalytic Properties of Transglutaminases;" *Advances in Enzymology*; vol. 38; 1973; pp. 109-191.
J.E. Folk, et al.; "The ε-(γ-Glutamyl)lysine Crosslink and the Catalytic Role of Transglutaminases;" *Advances in Protein Chemistry*; vol. 31; 1977; pp. 1-133.
K. Washizu, et al.; "Molecular Cloning of the Gene for Microbial Transglutaminase from *Strepoverticillium* and Its Expression in *Streptomyces lividans*;" *Biosci. Biotech. Biochem.*; vol. 58; No. 1; 1994; pp. 82-87.
D.J. Ballance, et al; "Development of a high-frequency transforming vector for *Aspergillus nidulans*;" *Gene*; vol. 36; 1985; pp. 321-331.

* cited by examiner

*Primary Examiner*—Rebecca E. Prouty
*Assistant Examiner*—Iqbal Chowdhury
(74) *Attorney, Agent, or Firm*—Kratz, Quintos & Hanson, LLP

(57) ABSTRACT

It is intended to provide a strain capable of producing transglutaminase at a high efficiency; and a process for producing transglutaminase by using this strain. A structural gene from *Streptomyces mobaraensis* and a promoter and a terminator acting on this structural gene are externally transferred into *Streptomyces mobaraensis* to give a transformant. Transglutaminase is produced by culturing this transformant.

28 Claims, 7 Drawing Sheets

Fig.3

Sequence Range: 1 to 669

Bases 1-669 of SEQ ID NO: 2

```
            10         20         30         40         50         60
        GATCTTCCGG GACATCTGAG GCGCCGGAGG CGATCCGAGG CGCCCGAGGC GTCTGCGCGA 70         80         90        100        110        120
        AGGGCGCCGC CGTGCCGTCC ATCCCCGTCC GCGTCGACGC GGGCCGGGAG GGGGTGCGGC 130        140        150        160        170        180
        GGCGCCCTTC GGCTGTGTGG ACGAAGCGTC GGGTCGGAGG GGCGGCCGGA TATCGTCCTT 190        200        210        220        230        240
        GGGGCGGGGT GGCCGGAATT GCCGCCATGG TGTTGCCGGG GAATCGACCC GAAGACATGA 250        260        270        280        290        300
        TCACTTCTCG TATCCACCCG ATCACGTATC CGGGAGTCGA GAAGTGTTAC GCCGTGCCCC 310        320        330        340        350        360
        TGTCCGCGTC CTCACCCCTG TCGCCGTGAC AGCGACCCGC GTTCTTCCAC TCGCACGGAC 370        380        390        400        410        420
        GGCCCCACAG GACCTTTCGG CCCGGGCTCG CCCCGCCGCC TCGGTGACGG CCTCCGAATA 430        440        450        460        470        480
        ACGCGGCCGC CGGGGCCTCG GCCGGTTGAC CGATCCGGGT CACGCGCCCC GCCGGGCGGG 490        500        510        520        530        540
        CGGCCACGTC CGGTCTCGCC CCGCCCGACA TCGGCTGCGA CTGCCTTCGC TCGCACTTCT 550        560        570        580        590        600
        TCCCGCCTCC CGGCCGCGTT TTTCCGCCGC CGAAGGTGCG GCGACGCGTA CCGAATCCCC 610        620        630        640        650        660
        CTTCATCGCG ACGTGCTTCC GCACGGCCGC GTTCAACGAT GTTCCACGAC AAAGGAGTTG

CAGGTTTCC
```

Bases 1-1287 of SEQ ID NO:2

Fig.4

```
GATCTTCCGG GACATCTGAG GCGCCGGAGG CGATCCGAGG CGCCCGACGC GTCTGCGCGA  60
AGGGCGCCGC CGTGCCGTCC ATCCCCGTCC GCGTCGACGC GGGCCGGCAG GGGGTGCGGC 120
GGCGCCCTTC GGCTGTGTGG ACGAAGCGTC GGGTCGGAGG GGCGGCCCGA TATCGTCCTT 180
GGGGCGGGGT GGCCGGAATT GCCGCCATGG TGTTGCCGGG GAATCGACCC GAAGACATGA 240
TCACTTCTCG TATCCACCCG ATCACGTATC CGGGAGTCGA GAAGTGTTAC GCCGTGCCCC 300
TGTCCGCGTC CTCACCCCTG TCGCCGTGAC AGCGACCCGC GTTCTTCCAC TCGCACGGAC 360
GGCCCACAG GACCTTTCGG CCCGGGCTCG CCCCGCCGCC TCGGTGACGG CCTCCGAATA 420
ACGCGGCCGC CGGGGCCTCG GCCGGTTGAC CGATCCGGGT CACGCCCCC GCCGGGCGGG 480
CGGCCACGTC CGGTCTCGCC CCGCCCGACA TCGGCTGCGA CTGCCTTCGC TCGCACTTCT 540
TCCCGCCTCC CGGCCGCGTT TTTCCGCCGC CGAAGGTGCG GCGACGCGTA CCGAATCCCC 600
CTTCATCGCG ACGTGCTTCC GCACGGCCGC GTTCAACGAT GTTCCACGAC AAAGGAGTTG 660
```

CAGGTTTCC ATG CGC ATA CGC CGG AGA GCT CTC GTC TTC GCC ACT ATG AGT
          Met Arg Ile Arg Arg Arg Ala Leu Val Phe Ala Thr Met Ser>
           1               5              10

720
GCG GTG TTA TGC ACC GCC GGA TTC ATG CCG TCG GCC GGC GAG GCC GCC
Ala Val Leu Cys Thr Ala Gly Phe Met Pro Ser Ala Gly Glu Ala Ala>

780
GCC GAC AAT GGC GCG GGG GAA GAG ACG AAG TCC TAC GCC GAA ACC TAC
Ala Asp Asn Gly Ala Gly Glu Glu Thr Lys Ser Tyr Ala Glu Thr Tyr>

840
CGC CTC ACG GCG GAT GAC GTC GCG AAC ATC AAC GCG CTC AAC GAA AGC
Arg Leu Thr Ala Asp Asp Val Ala Asn Ile Asn Ala Leu Asn Glu Ser>

900
GCT CCG GCC GCT TCG AGC GCC GGC CCG TCG TTC CGG GCC CCC GAC TCC
Ala Pro Ala Ala Ser Ser Ala Gly Pro Ser Phe Arg Ala Pro Asp Ser>

GAC GAC AGG GTC ACC CCT CCC GCC GAG CCG CTC GAC AGG ATG CCC GAC
Asp Asp Arg Val Thr Pro Pro Ala Glu Pro Leu Asp Arg Met Pro Asp>

960
CCG TAC CGT CCC TCG TAC GGC AGG GCC GAG ACG GTC GTC AAC AAC TAC
Pro Tyr Arg Pro Ser Tyr Gly Arg Ala Glu Thr Val Val Asn Asn Tyr>

1020
ATA CGC AAG TGG CAG CAG GTC TAC AGC CAC CGC GAC GGC AGG AAG CAG
Ile Arg Lys Trp Gln Gln Val Tyr Ser His Arg Asp Gly Arg Lys Gln>

1080
CAG ATG ACC GAG GAG CAG CGG GAG TGG CTG TCC TAC GGC TGC GTC GGT
Gln Met Thr Glu Glu Gln Arg Glu Trp Leu Ser Tyr Gly Cys Val Gly>

1140
GTC ACC TGG GTC AAT TCG GGT CAG TAC CCG ACG AAC AGA CTG GCC TTC
Val Thr Trp Val Asn Ser Gly Gln Tyr Pro Thr Asn Arg Leu Ala Phe>

GCG TCC TTC GAC GAG GAC AGG TTC AAG AAC GAG CTG AAG AAC GGC AGG
Ala Ser Phe Asp Glu Asp Arg Phe Lys Asn Glu Leu Lys Asn Gly Arg>

1200
CCC CGG TCC GGC GAG ACG CGG GCG GAG TTC GAG GGC CGC GTC GCG AAG
Pro Arg Ser Gly Glu Thr Arg Ala Glu Phe Glu Gly Arg Val Ala Lys>

1260
GAG AGC TTC GAC GAG GAG AAG GGC TTC CAG CGG GCG CGT GAG GTG GCG
Glu Ser Phe Asp Glu Glu Lys Gly Phe Gln Arg Ala Arg Glu Val Ala>

Fig.5　　　　　　　　　Bases 1288-2393 of SEQ ID NO: 2

```
                                          1320
TCC GTC ATG AAC AGG GCC CTG GAG AAC GCC CAC GAC GAG AGC GCT TAC
Ser Val Met Asn Arg Ala Leu Glu Asn Ala His Asp Glu Ser Ala Tyr>
                                                        1380
CTC GAC AAC CTC AAG AAG GAA CTG GCG AAC GGC AAC GAC GCC CTG CGC
Leu Asp Asn Leu Lys Lys Glu Leu Ala Asn Gly Asn Asp Ala Leu Arg>

AAC GAG GAC GCC CGT TCC CCG TTC TAC TCG GCG CTG CGG AAC ACG CCG
Asn Glu Asp Ala Arg Ser Pro Phe Tyr Ser Ala Leu Arg Asn Thr Pro>
        1440
TCC TTC AAG GAG CGG AAC GGA GGC AAT CAC GAC CCG TCC AGG ATG AAG
Ser Phe Lys Glu Arg Asn Gly Gly Asn His Asp Pro Ser Arg Met Lys>
                1500
GCC GTC ATC TAC TCG AAG CAC TTC TGG AGC GGC CAG GAC CGG TCG AGT
Ala Val Ile Tyr Ser Lys His Phe Trp Ser Gly Gln Asp Arg Ser Ser>
                        1560
TCG GCC GAC AAG AGG AAG TAC GGC GAC CCG GAC GCC TTC CGC CCC GCC
Ser Ala Asp Lys Arg Lys Tyr Gly Asp Pro Asp Ala Phe Arg Pro Ala>
                                                1620
CCG GGC ACC GGC CTG GTC GAC ATG TCG AGG GAC AGG AAC ATT CCG CGC
Pro Gly Thr Gly Leu Val Asp Met Ser Arg Asp Arg Asn Ile Pro Arg>

AGC CCC ACC AGC CCC GGT GAG GGA TTC GTC AAT TTC GAC TAC GGC TGG
Ser Pro Thr Ser Pro Gly Glu Gly Phe Val Asn Phe Asp Tyr Gly Trp>
        1680
TTC GGC GCC CAG ACG GAA GCG GAC GCC GAC AAG ACC GTC TGG ACC CAC
Phe Gly Ala Gln Thr Glu Ala Asp Ala Asp Lys Thr Val Trp Thr His>
                                1740
GGA AAT CAC TAT CAC GCG CCC AAT GGC AGC CTG GGT GCC ATG CAT GTC
Gly Asn His Tyr His Ala Pro Asn Gly Ser Leu Gly Ala Met His Val>
                                        1800
TAC GAG AGC AAG TTC CGC AAC TGG TCC GAG GGT TAC TCG GAC TTC GAC
Tyr Glu Ser Lys Phe Arg Asn Trp Ser Glu Gly Tyr Ser Asp Phe Asp>
                                                        1860
CGC GGA GCC TAT GTG ATC ACC TTC ATC CCC AAG AGC TGG AAC ACC GCC
Arg Gly Ala Tyr Val Ile Thr Phe Ile Pro Lys Ser Trp Asn Thr Ala>

CCC GAC AAG GTA AAG CAG GGC TGG CCG TGA TGTGAGC GGGGTGGACG
Pro Asp Lys Val Lys Gln Gly Trp Pro ***>
            1920
GGAGCCGGTT GCCCGGCTCC CCTCCACCCT CTCCCCCGCC ACCACGAAAG TCGCTACAGC
                1980
TCGTGTCCCG TCGTGCTGTC GACCTGCGCC GGGAGTTCGC CCTCGTGGCG GTCGCCCGTC
                2040
GTCGGGGTGC CCGTGGGTTC GAACATGAGG ATGGAGGCGC CCGGGGAGGA CGGCTTGTGT
            2100
TCGGTGCCCT TGGGCACCAC GAAGGTGTCG CCCTTGTGCA GGCGCACCGT GTGTTCCGTT
                2160
CCGTCGGAGT CGCGGAGCGC CACGTCGAAG CGGCCGTCCA GGACGAGGAA GAACTCGTCG
                2220
GTGTCCTCGT GGACGTGCCA GACGTGCTCG CCTCGGGTGT GGGCGACGCG GACGTCGTAG
            2280
TCGTTCATGC GGGCGACGAT GCGCGGGCTG TAGACGTCGT CGAAGGAGGC GAGGGCCTTG
                2340
GCGACGTTGA CGGGCTCGGT GTCGTTCATG GTCCGAGTCT CGGCGGGAGC CCGCCGCGGC
GTC
```

Fig.6

|  | Amount of BTG in culture supernatant |
|---|---|
| ABL-1:pUJ51BD/*S.lividans* 3131TS | 0.7 g/L |
| ABM-1:pUJ51BD/*S.mobaraensis* S-8112 | 0.5 g/L |

1 S.lividans

2 ABL-1:pUJ51BD／S.lividans

3 Purified BTG

4 S.mobaraensis

5 ABM-1:pUJ51BD／S.mobaraensis

SEQUENCE LISTING

```
<160> NUMBER OF SEQ ID NOS: 7

<210> SEQ ID NO 1
<211> LENGTH: 1224
<212> TYPE: DNA
<213> ORGANISM: Streptomyces mobaraensis
<220> FEATURE:
<221> NAME/KEY: source
<222> LOCATION: (1)..(1224)
<223> OTHER INFORMATION: transglutaminase gene

<400> SEQUENCE: 1
atgcgcatac gccggagagc tctcgtcttc gccactatga gtgcggtgtt atgcaccgcc        60
ggattcatgc cgtcggccgg cgaggccgcc gccgacaatg gcgcggggga agagacgaag       120
tcctacgccg aaacctaccg cctcacggcg gatgacgtcg cgaacatcaa cgcgctcaac       180
gaaagcgctc cggccgcttc gagcgccggc ccgtcgttcc gggcccccga ctccgacgac       240
agggtcaccc ctcccgccga gccgctcgac aggatgcccg acccgtaccg tccctcgtac       300
ggcagggccg agacggtcgt caacaactac atacgcaagt ggcagcaggt ctacagccac       360
cgcgacggca ggaagcagca gatgaccgag gagcagcggg agtggctgtc ctacggctgc       420
gtcggtgtca cctgggtcaa ttcgggtcag tacccgacga acagactggc cttcgcgtcc       480
ttcgacgagg acaggttcaa gaacgagctg aagaacggca ggcccggtc cggcgagacg       540 cgggcggagt tcgagggccg cgtcgcgaag gagagcttcg acgaggagaa gggcttccag       600
cgggcgcgtg aggtggcgtc cgtcatgaac agggccctgg agaacgccca cgacgagagc       660
gcttacctcg acaacctcaa gaaggaactg gcgaacggca acgacgccct gcgcaacgag       720
gacgcccgtt ccccgttcta ctcggcgctg cggaacacgc cgtccttcaa ggagcggaac       780
ggaggcaatc acgacccgtc caggatgaag gccgtcatct actcgaagca cttctggagc       840
ggccaggacc ggtcgagttc ggccgacaag aggaagtacg gcgacccgga cgccttccgc       900
cccgccccgg gcaccggcct ggtcgacatg tcgagggaca ggaacattcc gcgcagcccc       960
```

```
accagccccg gtgagggatt cgtcaatttc gactacggct ggttcggcgc ccagacggaa    1020
gcggacgccg acaagaccgt ctggacccac ggaaatcact atcacgcgcc caatggcagc    1080
ctgggtgcca tgcatgtcta cgagagcaag ttccgcaact ggtccgaggg ttactcggac    1140
ttcgaccgcg gagcctatgt gatcaccttc atccccaaga gctggaacac cgccccccgac   1200 aaggtaaagc agggctggcc gtga                                           1224
```

```
<210> SEQ ID NO 2
<211> LENGTH: 2393
<212> TYPE: DNA
<213> ORGANISM: Streptomyces mobaraensis

<400> SEQUENCE: 2
gatcttccgg gacatctgag gcgccggagg cgatccgagg cgcccgaggc gtctgcgcga      60
agggcgccgc cgtgccgtcc atccccgtcc gcgtcgacgc gggccgggag ggggtgcggc     120 ggcgccttc  ggctgtgtgg acgaagcgtc gggtcggagg ggcggccgga tatcgtcctt     180
ggggcggggt ggccggaatt gccgccatgg tgttgccggg gaatcgaccc gaagacatga     240
tcacttctcg tatccacccg atcacgtatc cgggagtcga gaagtgttac gccgtgcccc     300
tgtccgcgtc ctcacccctg tcgccgtgac agcgacccgc gttcttccac tcgcacggac     360
ggccccacag gacctttcgg cccgggctcg ccccgccgcc tcggtgacgg cctccgaata     420
acgcggccgc cggggcctcg gccggttgac cgatccgggt cacgcgcccc gccgggcggg     480
cggccacgtc cggtctcgcc ccgcccgaca tcggctgcga ctgccttcgc tcgcacttct     540
tcccgcctcc cggccgcgtt tttcgccgc cgaaggtgcg cgacgcgta ccgaatcccc       600 cttcatcgcg acgtgcttcc gcacggccgc gttcaacgat gttccacgac aaaggagttg     660
caggtttcca tgcgcatacg ccggagagct ctcgtcttcg ccactatgag tgcggtgtta     720
tgcaccgccg gattcatgcc gtcggccggc gaggccgccg ccgacaatgg cgcgggggaa     780
gagacgaagt cctacgccga aacctaccgc ctcacggcgg atgacgtcgc gaacatcaac     840
gcgctcaacg aaagcgctcc ggccgcttcg agcgccggcc cgtcgttccg ggcccccgac     900
tccgacgaca gggtcacccc tccgccgag ccgctcgaca ggatgcccga cccgtaccgt      960
ccctcgtacg gcagggccga gacggtcgtc aacaactaca tacgcaagtg gcagcaggtc    1020
tacagccacc gcgacggcag gaagcagcag atgaccgagg agcagcggga gtggctgtcc    1080
tacggctgcg tcggtgtcac ctgggtcaat tcgggtcagt acccgacgaa cagactggcc    1140
ttcgcgtcct tcgacgagga caggttcaag aacgagctga agaacggcag gccccggtcc    1200
ggcgagacgc gggcggagtt cgaggccgc gtcgcgaagg agagcttcga cgaggagaag     1260
ggcttccagc gggcgcgtga ggtggcgtcc gtcatgaaca gggcccctgga gaacgcccac   1320 gacgagagcc cttacctcga caacctcaag aaggaactgg cgaacggcaa cgacgccctg    1380
cgcaacgagg acgcccgttc cccgttctac tcggcgctgc ggaacacgcc gtccttcaag    1440
gagcggaacg gaggcaatca cgaccccgtcc aggatgaagg ccgtcatcta ctcgaagcac   1500
ttctgggagc gccaggaccg gtcgagttcg gccgacaaga ggaagtacgg cgacccggac    1560
gccttccgcc ccgccccggg caccggcctg tcgacatgt cgagggacag gaacattccg     1620
cgcagcccca ccagccccgg tgagggattc gtcaatttcg actacggctg gttcggcgcc    1680
cagacggaag cggacgccga caagaccgtc tggacccacg gaaatcacta tcacgcgccc    1740
aatggcagcc tgggtgccat gcatgtctac gagagcaagt tccgcaactg gtccgagggt    1800
```

```
tactcggact tcgaccgcgg agcctatgtg atcaccttca tccccaagag ctggaacacc    1860
gcccccgaca aggtaaagca gggctggccg tgatgtgagc ggggtggagg ggagccggtt    1920
gcccggctcc cctccaccct ctcccccgcc accacgaaag tcgctacagc tcgtgtcccg    1980
tcgtgctgtc gacgtgcgcc gggagttcgc cctcgtggcg gtcgcccgtc gtcggggtgc    2040
ccgtgggttc gaacatgagg atggaggcgc ccggggagga cggcttgtgt tcggtgccct    2100
tgggcaccac gaaggtgtcg cccttgtgca ggcgcaccgt gtgttccgtt ccgtcggagt    2160
cgcggagcgc cacgtcgaag cggccgtcca ggacgaggaa gaactcgtcg gtgtcctcgt    2220
ggacgtgcca gacgtgctcg cctcgggtgt gggcgacgcg gacgtcgtag tcgttcatgc    2280
gggcgacgat gcgcgggctg tagacgtcgt cgaaggaggc gagggccttg gcgaggttga    2340
cgggctcggt gtcgttcatg gtccgagtct cggcgggagc ccgccgcggc gtc           2393
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
acaccgcact catagtggcg                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
tccgtgcgag tggaagaacg                                                 20

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 5
gacggcctcc gaataac                                                    17

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
atgtcgaggg acaggaac                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Primer -continued

```
<400> SEQUENCE: 7
caccacgaaa gtcgctac                                                      18
```

TRANSGLUTAMINASE-PRODUCING STRAIN

TECHNICAL FIELD

The present invention relates to a strain producing transglutaminase derived from actinomycetes and a process for producing transglutaminase by using the strain.

BACKGROUND ART

Transglutaminase is an enzyme which catalyzes an acyl transfer reaction of a γ-carboxy amide group of glutamine residue in a peptide chain. In particular, transglutaminase induces intramolecular or intermolecular formation of e-(γ-Gln)-Lys cross linking to an e-amino group of a lysine residue in a protein. The enzyme has been widely used for processing proteins by using this property in the fields of food and medicine.

Since a long time ago, animal-derived transglutaminase has been known. It has been reported that transglutaminase has been found in animals, for example, in the liver of guinea pigs and in organs and blood of mammals (Connellan et al., Journal of Biological Chemistry, vol. 246, No. 4, pp. 1093-1098 (1971)), Folk et al., Advances in Enzymology, vol. 38, pp. 109-191 (1973); and Folk et al., Advances in Protein Chemistry, vol. 31, pp. 1-133 (1977)), and its enzymological properties have been studied. On the other hand, a different type of transglutaminase, which is not dependent upon calcium ($Ca^{2+}$) and is therefore different from the above-mentioned animal-derived transglutaminase, has been found. Specifically, transglutaminase has been isolated and identified from *Streptomyces mobaraensis* [old name: *Streptoverticillium mobaraense*] IFO 13819 (Japanese Patent Unexamined Publication No. S64-27471), *Streptomyces griseocarneus* [old name: *Streptoverticillium griseocarneum*)] IFO 12776, and *Streptomyces cinnamoneus*) [old name: *Streptoverticillium cinnamoneum*)] IFO 12852 (Japanese Patent Unexamined Publication No. 2001-186884), etc.

DISCLOSURE OF INVENTION

Conventionally, since transglutaminase has been produced via extraction and isolation, etc. from animals, micro-organisms, and the like, that are present in nature, there have been many problems to be solved such as a low production yield and an expensive production cost, etc. Meanwhile, as to transglutaminase derived from micro-organisms, process for producing by using genetic recombination has been intensively studied. However, according to the first report of a process using genetic recombination (Biosci. Biotech. Biochem., 58,82-87 (1994), Japanese Patent Unexamined Publication No. H5-199883), the production amount was about 0.1 mg/l, which was far from industrial production level. Furthermore, according to the recent report (Japanese Patent Unexamined Publication No. 2001-186884), although the production level was improved to some extent, two-week microbial culture resulted in the productivity of only about 40 to 50 mg/l. Also, in this case, it cannot be said that sufficient productivity is obtained.

The present invention was made on the basis of the above-mentioned background, and the object of the present invention is to provide a strain capable of producing transglutaminase at a high efficiency and a process for producing transglutaminase using the strain.

In order to solve the above-mentioned problems, the present inventors have eagerly investigated. That is to say, for expressing transglutaminase derived from actinomycetes, the present inventors have investigated the combination of a transglutaminase structural gene, a promoter, a vector and host actinomycetes. As a result, the present inventors have succeeded in obtaining transformant having extremely high productivity of transglutaminase and have completed the present invention. The present invention provides the following configurations.

[1] A transformant of *Streptomyces mobaraensis*, comprising a structural gene of transglutaminase derived from *Streptomyces mobaraensis* and a promoter and a terminator acting on the structural gene, which are externally introduced.

[2] The transformant of *Streptomyces mobaraensis* according to [1], wherein the promoter is a promoter of transglutaminase derived from *Streptomyces mobaraensis*.

[3] The transformant of *Streptomyces mobaraensis* described in [1] or [2], wherein the terminator is a terminator of transglutaminase derived from *Streptomyces mobaraensis*.

[4] The transformant of *Streptomyces mobaraensis* described in any of [1] to [3], wherein the structural gene comprises a sequence set forth in SEQ ID NO: 1 or a sequence obtained by modifying a part of the sequence, the sequence encoding transglutaminase.

[5] A transformant of *Streptomyces mobaraensis* comprising a DNA fragment having an externally introduced sequence set forth in SEQ ID NO: 2 or sequence obtained by modifying a part of the sequence, the sequence encoding transglutaminase.

[6] The transformant of *Streptomyces mobaraensis* described in any of [1] to [5], which is a transformant of *Streptomyces mobaraensis* S-8112 or a mutant strain thereof.

[7] A process for producing transglutaminase, comprising the steps of:
  culturing transformant of *Streptomyces mobaraensis* comprising a structural gene of transglutaminase derived from *Streptomyces mobaraensis* and a promoter and a terminator acting on the structural gene, which are externally introduced, under the conditions where the structural gene can be expressed; and
  collecting the produced transglutaminase.

[8] The process for producing transglutaminase described in [7], wherein the promoter is a promoter of transglutaminase derived from *Streptomyces mobaraensis*.

[9] The process for producing transglutaminase described in [7] or [8], wherein the terminator is a terminator of transglutaminase derived from *Streptomyces mobaraensis*.

[10] The process for producing the transglutaminase described in any of [7] to [9], wherein the structural gene comprises a sequence set forth in SEQ ID NO: 1 or a sequence obtained by modifying a part of the sequence, the sequence encoding transglutaminase.

[11] The process for producing transglutaminase described in any of [7] to [9], wherein the transformant of *Streptomyces mobaraensis* comprises a DNA fragment having an externally introduced sequence set forth in SEQ ID NO: 2 or sequence obtained by modifying a part of the sequence, the sequence encoding transglutaminase.

[12] The process for producing transglutaminase described in any of [7] to [11], wherein the transformant of *Streptomyces mobaraensis* is a transformant of *Streptomyces mobaraensis* S-8112 or a mutant strain thereof.

[13] A transformant of *Streptomyces lividans* comprising a structural gene of transglutaminase derived from *Streptomyces mobaraensis*, and a promoter and a terminator acting on the structural gene, which are externally introduced.

[14] The transformant of *Streptomyces lividans* described in [13], wherein the promoter is a promoter of transglutaminase derived from *Streptomyces mobaraensis*.

[15] The transformant of *Streptomyces lividans* described in [13] or [14], wherein the terminator is a terminator of transglutaminase derived from *Streptomyces mobaraensis*.

[16] The transformant of *Streptomyces lividans* described in any of [13] to [15], wherein the structural gene comprises a sequence set forth in SEQ ID NO: 1 or a sequence obtained by modifying a part of the sequence, the sequence encoding transglutaminase.

[17] A transformant of *Streptomyces lividans* comprising a DNA fragment having an externally introduced sequence set forth in SEQ ID NO: 2 or sequence obtained by modifying a part of the sequence, the sequence encoding transglutaminase.

[18] The transformant of *Streptomyces lividans* described in any of [13] to [17], which is a transformant of *Streptomyces lividans* 3131 or a mutant strain thereof.

[19] A process for producing transglutaminase, comprising the steps of:
culturing transformant of *Streptomyces lividans* comprising a structural gene of transglutaminase derived from *Streptomyces mobaraensis* and a promoter and a terminator acting on the structural gene, which are externally introduced, under the conditions where the structural gene can be expressed; and
collecting the produced transglutaminase.

[20] The process for producing transglutaminase described in [19], wherein the promoter is a promoter of transglutaminase derived from *Streptomyces mobaraensis*.

[21] The process for producing transglutaminase described in [19] or [20], wherein the terminator is a terminator of transglutaminase derived from *Streptomyces mobaraensis*.

[22] The process for producing transglutaminase described in any of [19] to [21], wherein the structural gene comprises a sequence set forth in SEQ ID NO: 1 or a sequence obtained by modifying a part of the sequence, the sequence encoding transglutaminase.

[23] The process for producing transglutaminase described in any of [19] to [21], wherein the transformant of *Streptomyces lividans* comprises a DNA fragment having an externally introduced sequence set forth in SEQ ID NO: 2 or a sequence obtained by modifying a part of the sequence, the sequence encoding transglutaminase.

[24] The process for producing transglutaminase described in any of [19] to [23], wherein the transformant of *Streptomyces lividans* is a transformant of *Streptomyces lividans* 3131 or a mutant strain thereof.

BRIEF DESCRIPTION OF DRAWINGS

FIG. 3 shows a base sequence of a promoter region of a transglutaminase (BTG) gene determined in Examples.

FIG. 4 shows a base sequence of a promoter region and a part of a structural gene of a transglutaminase (BTG) gene.

FIG. 5 shows a base sequence of a part of a structural gene and a terminator region of a transglutaminase (BTG) gene.

FIG. 6 is a table summarizing measurement results of the amount of BTG in a culture supernatant of transformants ABL-1 and ABM-1, respectively.

BEST MODE FOR CARRYING OUT THE INVENTION

Figure 1:
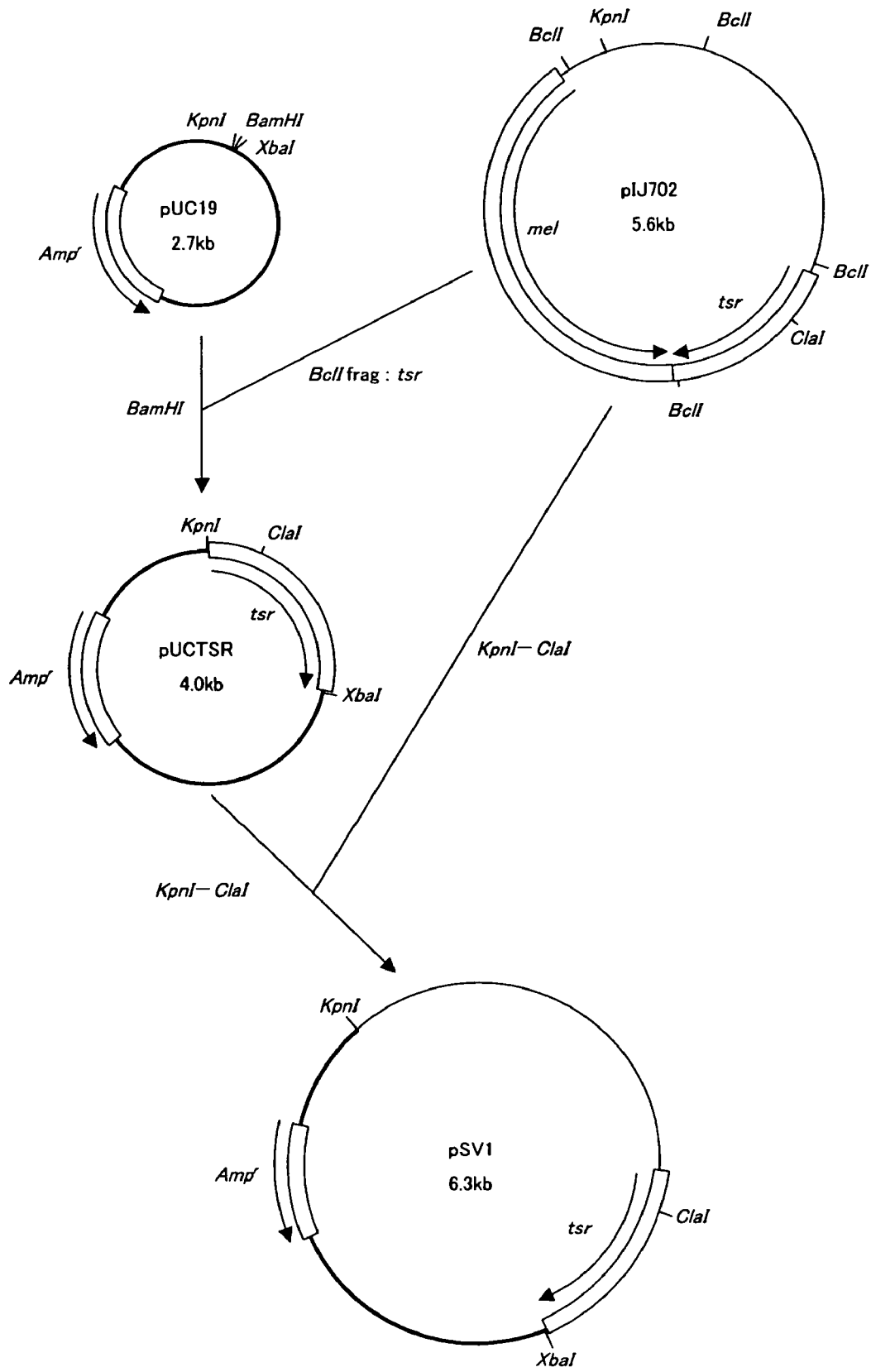
FIG. 1 shows a method of constructing a shuttle vector pSV1 in Examples.

Hereinafter, the detail configuration of the present invention will be described. The present invention provides a transformant actinomycetes (*Streptomyces mobaraensis* or *Streptomyces lividans*) comprising a structural gene of transglutaminase derived from *Streptomyces mobaraensis*, and a promoter and a terminator acting on the structural gene, which are externally introduced.

Herein, the kind of structural gene of transglutaminase is not particularly limited as long as it is derived from *Streptomyces mobaraensis*. For example, a structural gene of transglutaminase carried by *Streptomyces mobaraensis* S-8112 can be used. A specific example of the structural gene can include a DNA consisting of a base sequence set forth in SEQ ID NO: 1. Note here that *Streptomyces mobaraensis* S-8112 is deposited (accession number: FERM P-18980) with the following depositary agency.

Depositary agency
Name: National Institute of Advanced Industrial Science and Technology, International Patent Organism Depositary
Address: Chuo No. 6, 1-3, Higashi 1-chome, Tsukuba-shi, Ibaraki-ken, 305-8566, Japan
Deposition date: Aug. 20, 2002

The structural gene of transglutaminase can be obtained as follows, for example. That is to say, a genomic DNA library of *Streptomyces mobaraensis* is constructed, and this library is screened by using a probe specific to the structural gene of transglutaminase. Then, an inserted DNA fragment is obtained by restriction enzyme treatment from the selected clone. Note here that the structural gene of transglutaminase can be prepared also by a well-known synthetic method using a PCR method, etc.

DNA obtained by modifying a part of DNA set forth in SEQ ID NO: 1 (hereinafter, also referred to as "modified DNA") can be also used as the structural gene of the present invention as long as a protein encoded thereby has a transglutaminase activity. Note here that it is preferable that the level of the transglutaminase activity is as high as possible. For example, it is preferable that the transglutaminase activity is the same level as the transglutaminase activity of a protein encoded by the DNA consisting of the sequence set forth in SEQ ID NO: 1.

A specific example of the modified DNA can include a DNA hybridizing to the DNA having the sequence set forth in SEQ ID NO: 1 under stringent conditions and encoding a protein having a transglutaminase activity. Note here that "stringent conditions" herein denote conditions where so-called specific hybrid is formed and non-specific hybrid is not formed. For example, stringent conditions includes conditions where incubation is carried out by using a hybridization solution (50% formamide, 10 SSC (0.15 M NaCl, 15 mM sodium citrate, pH 7.0), 5× Denhardt solution, 1% SDS, 10% dextran sulfate, 10 µg/ml denatured salmon sperm DNA, and 50 mM phosphoric acid buffer (pH 7.5)) at 42° C., followed by washing with 0.1×SSC and 0.1% SDS at 68° C. Further preferable stringent conditions can include conditions where a hybridization solution (50% formamide, 5×SSC (0.15M NaCl, 15 mM sodium citrate, pH 7.0), 1× Denhardt solution, 1% SDS, 10% dextran sulfate, 10 µg/ml denatured salmon sperm DNA, and 50 mM phosphoric acid buffer (pH 7.5)) is used.

Another example of the modified DNA can include DNA consisting of base sequence including substitution, deletion, insertion, addition or inversion of one or plurality of bases in a base sequence set forth in SEQ ID NO: 1 and encoding a protein having a transglutaminase activity. Mutation such as base substitution may be in a plurality of sites. Herein, "plurality" denotes 2 to 40, preferably 2 to 20, and more preferably 2 to 10 although it is different depending upon kinds or positions of amino acids encoded by bases to be mutated. Note here that such modification includes introduction of a restriction site into 5' end, 3' end or other sites, or addition of a sequence encoding a signal peptide.

The above-mentioned modified DNA can be obtained by genetically modifying DNA having a sequence set forth in SEQ ID NO: 1 so that amino acid residues at a certain cite includes substation, deletion, insertion, addition or inversion by the use of, for example, a site specific mutation method. Also, the above-mentioned modified DNA can be obtained by using a well-known mutation process including processing *Streptomyces mobaraensis* carrying a transglutaminase gene with ultraviolet light and then isolating the structural gene of the modified transglutaminase, and the like.

Note here that above-mentioned mutation such as substitution, deletion, insertion, addition, inversion, or the like, of bases includes naturally occurring mutation, for example, mutation based on individual difference of *Streptomyces mobaraensis*.

For example, when naturally existing *Streptomyces mobaraensis* has such a modified DNA, genome (chromosome) DNA is extracted from the strain and processed with an appropriate restriction enzyme, followed by selecting and isolating DNA that hybridizing under stringent conditions in a screening with the use of the DNA of SEQ ID NO: 1 or a part of the DNA as a probe. Thus, a modified DNA can be obtained.

A promoter acting on the above-mentioned structural gene can be employed. Preferably, a promoter of transglutaminase derived from *Streptomyces mobaraensis* is employed. Further preferably, a promoter whose origin is the same as that of the structural gene to be used is employed. For example, when the structural gene of transglutaminase is obtained from *Streptomyces mobaraensis* as mentioned above, a DNA fragment including also a promoter region thereof in addition to the structural gene is obtained and this DNA fragment can be used as the structural gene and the promoter of the present invention.

Also as to the terminator, a terminator acting on the above-mentioned structural gene is employed. Preferably, a terminator of transglutaminase derived from *Streptomyces mobaraensis* is employed. Further preferably, a terminator whose origin is the same as that of the structural gene to be used is employed. For example, when the structural gene of transglutaminase is obtained from *Streptomyces mobaraensis* as mentioned above, a DNA fragment including also a terminator region thereof in addition to the structural gene is obtained and this DNA fragment can be used as the structural gene and the terminator of the present invention.

Herein, it is particularly preferable that all of the promoter, structural gene and terminator are derived from the same *Streptomyces mobaraensis*. An example of such embodiment includes the case of using a host *Streptomyces mobaraensis* containing a DNA fragment having a sequence set forth in SEQ ID NO: 2. Such a DNA fragment can be prepared so as to include the promoter and terminator regions in addition to the structural gene when the structural gene of transglutaminase is obtained from *Streptomyces mobaraensis* as mentioned above.

Herein, even if the DNA consisting of the sequence set forth in SEQ ID NO: 2 is a DNA obtained by modifying a part of the sequence (modified DNA), such a DNA can be used as long as a protein encoded thereby has a transglutaminase activity. Note here that it is preferable that the level of the transglutaminase activity is as high as possible. For example, it is preferable that the transglutaminase activity is the same level as the transglutaminase activity of protein encoded by the DNA consisting of the sequence set forth in SEQ ID NO: 2.

As in the case of the DNA of SEQ ID NO: 1, a specific example of the modified DNA can include a DNA hybridizing the DNA having the sequence set forth in SEQ ID NO: 2 under stringent conditions and encoding a protein having the transglutaminase activity, and DNA consisting of base sequence including substitution, deletion, insertion, addition or inversion of one or a plurality of bases in the base sequence set forth in SEQ ID NO: 2 and encoding a protein having a transglutaminase activity. Besides, the range capable of being modified, a preparing method of modified DNA, and the like, are the same as those of the DNA set forth in SEQ ID NO: 1.

A transformant of actinomycetes (*Streptomyces mobaraensis* or *Streptomyces lividans*) into which the above-mentioned structural gene, promoter and terminator were externally introduced is produced by transforming a host actinomycete (*Streptomyces mobaraensis* or *Streptomyces lividans*) with the use of an expression vector containing the structural gene, etc.

As *Streptomyces mobaraensis* to be used for transformation, for example, *Streptomyces mobaraensis* S-8112 (accession number: FERM P-18980) or the mutant strain thereof can be used. On the other hand, as *Streptomyces lividans*, for example, *Streptomyces lividans* 3131 (ATCC 35287) or the mutant strain thereof can be used. For producing the mutant strain, for example, a well-known method such as ultraviolet irradiation can be used.

For constructing the expression vector, a well-known vector such as commercially available vector that can be used for transformation of actinomycetes can be used. For example, an expression vector can be constructed by combining a plasmid, pUC19, pBR322, pBluescript, etc., using *Escherichia coli* as a host and a plasmid, pIJ702, etc. carried by *Streptomyces lividans* 3131, using actinomycetes as a host. Specific examples of the expression plasmid are shown as follows. First of all, a shuttle vector having both replication origin of *Escherichia coli* and replication origin of actinomycetes is constructed by using pUC19 and pIJ702. On the other hand, DNA fragment containing a promoter, a structural gene and a terminator of transglutaminase is isolated from *Streptomyces mobaraensis*, and inserted into an appropriate restriction site of pUC19. Then, pIJ702 and the above-mentioned shuttle vector are used to insert a tsr (thiostrepton-resistance) gene into this plasmid. Thus, an expression vector containing a replication origin of *Escherichia coli*, $Amp^r$(ampicillin-resistance) gene, a replication origin of actinomycetes and a tsr(thiostrepton-resistance) gene, as well as a promoter, a structural gene and a terminator of transglutaminase is obtained.

Restriction enzyme treatment, insertion of a DNA fragment, and the like, for constructing a vector can be carried out by a routine method.

Note here that an expression vector including such a structural gene of transglutaminase derived from *Streptomyces mobaraensis*, and a promoter and terminator acting on the structural gene can be used for transformation of microorganisms belonging to *Streptomyces* other than *Streptomyces mobaraensis*.

The transformation of actinomycetes (*Streptomyces mobaraensis* or *Streptomyces lividans*) using the expression vector constructed as mentioned above can be carried out by a method of introducing an expression vector into a protoplast host actinomycetes. It is preferable that such a transformation is carried out under the conditions where actinomycetes as a host can be grown. According to the investigation of the present inventors, the efficiency of transformation by such a method is remarkably increased. Other conditions and operation methods, etc. can be carried out by appropriately selecting the conditions and methods employed in a routine method (for example, a method by Turner et al. (Gene, 36, 321-331(1985)). Herein, "the conditions where actinomycetes as a host can be grown" denotes conditions in which a reaction solution contains nutrition necessary for growing actinomycetes. Specific example of such conditions includes conditions in which a reaction solution contains meat extracts, yeast extracts, and/or peptone (including polypeptone, tripeptone, casein peptone, and the like). In order to achieve higher transformation efficiency, it is further preferable that both step of allowing the host to be a protoplast and a step of introducing a vector into the protoplast host are carried out under such conditions.

The selection of transformant can be carried out by using a selection marker such as a tsr gene, which was incorporated in the expression vector in advance, can be used.

Transglutaminase can be produced by culturing the selected transformant, that is, a host actinomycetes (*Streptomyces mobaraensis* or *Streptomyces lividans*) in which a structural gene derived from *Streptomyces mobaraensis*, a promoter and a terminator of transglutaminase are externally introduced, under the conditions where the structural gene of transglutaminase can be expressed. As a medium for culturing the transformant, a medium containing a carbon source, a nitrogen source and, inorganic chlorine (inorganic ion) as appropriate can be used. In order to promote the growth of transformant, a medium, to which vitamin, amino acid, and the like is added, can be used. Examples of the carbon source can include, for example, glucose, starch, dextrin, and the like. Examples of the nitrogen source can include, for example, polypeptone, yeast extracts, meat extracts, and the like. Examples of inorganic chlorine can include dipotassium phosphate, magnesium sulfate, sodium chloride, potassium chloride, and the like.

The culture temperature for culturing the transformant is, for example, in the range from 15° C. to 37° C., and preferably in the range from 25° C. to 35° C. Furthermore, pH of the medium is adjusted to, for example, 5.0 to 8.0, and preferably 6.0 to 7.5.

Transglutaminase can be collected from a culture solution in which transformant was cultured for a predetermined time or the cell body. When transglutaminase is collected from the culture solution, transglutaminase can be obtained by removing insoluble substances via filtration and centrifugation of culture supernatant, followed by isolating and purifying via the combination of salting-out such as ammonium sulfate precipitation, dialysis, various chromatography, and the like. On the other hand, transglutaminase is collected from the cell body, for example, transglutaminase can be obtained by isolating and purifying as mentioned above after the cell body is crushed by pressure treatment, ultrasonic treatment, etc. Note here that after the cell body is collected from the culture solution in advance by filtration, centrifugation, and the like, the above-mentioned series of steps (crush, isolation, and purification of the cell body) may be carried out.

EXAMPLES

In Examples of the present invention, unless otherwise indicated, restriction enzymes and other enzymes for gene operation, products of Takara Shuzo Co., Ltd. or TOYOBO CO LTD were used. Note here that the reaction conditions of enzymes, etc. follows the appended instruction manual.

Example 1

Obtaining Actinomycetes Vector pIJ702

*Streptomyces lividans* 3131 (ATCC 35287) containing a plasmid pIJ702 was cultured under the following medium conditions at 30° C. for two days.

| YEME medium + 0.5% glycine + 50 µg/ml thiostrepton | |
|---|---|
| Yeast extracts | 3 g |
| Peptone | 5 g |
| Malt extracts | 3 g |
| Magnesium chloride | 1 g |
| Glucose | 10 g |
| Saccharose | 340 g |
| Glycine | 5 g |
| 50 mg/ml thiostrepton solution (SIGMA: dimethylsulfoxide solution) | 1 ml/L (pH 7.0) |

The 200 ml of cultured medium was centrifuged (12,000 g at 4° C. for 10 minutes) and the obtained cell body was suspended in 10 ml of solution consisting of 50 mM Tris-HCl (pH 8.0), 10 mM EDTA and 25% Sucrose (hereinafter, referred to as "TE-Sucrose"). Then, 2 ml of TE-Sucrose containing 30 mg/ml of lysozyme (Sigma Aldrich Japan K.K.) and 4 ml of 0.25 mM EDTA were added to the suspension, which was incubated at 37° C. for 30 minutes. After incubation, 2 ml of 20% SDS was added, further 5 ml of 5M NaCl was added and gently stirred, and then incubated at 0° C. over night.

Then, 30% polyethylene glycol 6000 was added to supernatant obtained by centrifugation (100,000 g at 4° C. for 40 minutes) so that the final concentration became 10% and incubated at 0° C. for 4.5 hours. Thereafter, it was centrifuged (900 g at 4° C. for 5 minutes) and the precipitate thus obtained was dissolved in a solution consisting of 10 mM Tris-HCl (pH 8.0), 1 mM EDTA and 50 mM NaCl. Then, to this were added 16.8 g of cesium chloride and 1.2 ml of a solution consisting of 10 mM Tris-HCl (pH 8.0) and 1 mM EDTA (hereinafter, referred to as "TE") in which ethidium bromide had been dissolved to the concentration of 10 mg/ml. The resulting mixture was centrifuged (1,300 g at room temperature for 15 minutes) to remove residues, and then centrifuged (230,000 g at 20° C. for 12 hours) again. After centrifugation, under ultraviolet irradiation, a plasmid DNA layer was obtained. Then, extraction with butanol saturated with TE was carried out so as to remove ethidium bromide. The extraction was repeated three times. The obtained plasmid DNA solution was subjected to dialysis over night at 4° C. using TE as an external dialysis solution. Then, extraction treatment was carried out once with TE-saturated phenol and twice with chloroform isoamyl alcohol. To this were added 1/10 volume of 3 M sodium acetate (pH 5.2) solution and 2 volumes of ethanol. After standing for 30 minutes at −80° C., the resulting mixture was centrifuged (12,000 g at 4° C. for 15 minutes) so as to collect precipitate. The precipitate was washed with 70% ethanol and dried. This was dissolved in 200 µl of TE. By the above-mentioned operation, the final DNA amount was about 10 µg.

Example 2

Obtaining Thiostrepton Sensitive Strain from *Streptomyces lividans* 3131 (ATCC 35287) Carrying pIJ702

*Streptomyces lividans* 3131 (ATCC 35287) containing pIJ702 was cultured at 30° C. for seven days using a YEME medium. Then, a culture solution was diluted to $10^5$ to $10^9$ times with the YEME medium. A 100 µl each of the diluted solution was inoculated on each of five plates containing a YEME agar medium (YEME medium supplemented with 1.5% agar). After culturing at 30° C. for a week, the cultured medium was replicated on the YEME agar medium containing 200 µg/ml of thiostrepton using RepliPlate™ Colony Transfer Pad (Takara Shuzo Co., Ltd.), and cultured again at 30° C. for a week. A strain, from which the plasmid pIJ702 was dropped to become a thiostrepton-sensitive strain, was selected to obtain *Streptomyces lividans* 3131-TS. This strain was used as a host for later transformation.

Example 3

Obtaining Shuttle Vector pSV1

Shuttle vector pSV1 was constructed by the method shown in FIG. 1. First of all, a DNA fragment obtained by digesting *E. coli* vector pUC19 (Takara Shuzo Co., Ltd.) with a restriction enzyme Bam HI and a DNA fragment containing tsr obtained by digesting actinomycetes vector pIJ702 with Bcl I (Takara Shuzo Co., Ltd.) were prepared. These DNA fragments were ligated to each other by using DNA Ligation Kit (Takara Shuzo Co., Ltd.) to produce pUCTSR. Then, a DNA fragment (long fragment) obtained by digesting pUCTSR with Kpn I and Cla I (Takara Shuzo Co., Ltd.) and a DNA fragment (short fragment) obtained by digesting pIJ702 with Kpn I and Cla I (Takara Shuzo Co., Ltd.) were prepared, and these DNA fragments were ligated to each other by using DNA Ligation Kit (Takara Shuzo Co., Ltd.) to transform to an *E. coli* DH5 strain (TOYOBO Co., Ltd.). A plasmid was obtained by ligating pUC19 fragment and pIJ702 fragment which are carried by the thus obtained transformant to obtain a shuttle vector pSV1. The shuttle vector pSV1 was used for the later operation.

Example 4

Manufacture of Transglutaminase Secretion Expression Plasmid pUJ51BD

Figure 2:
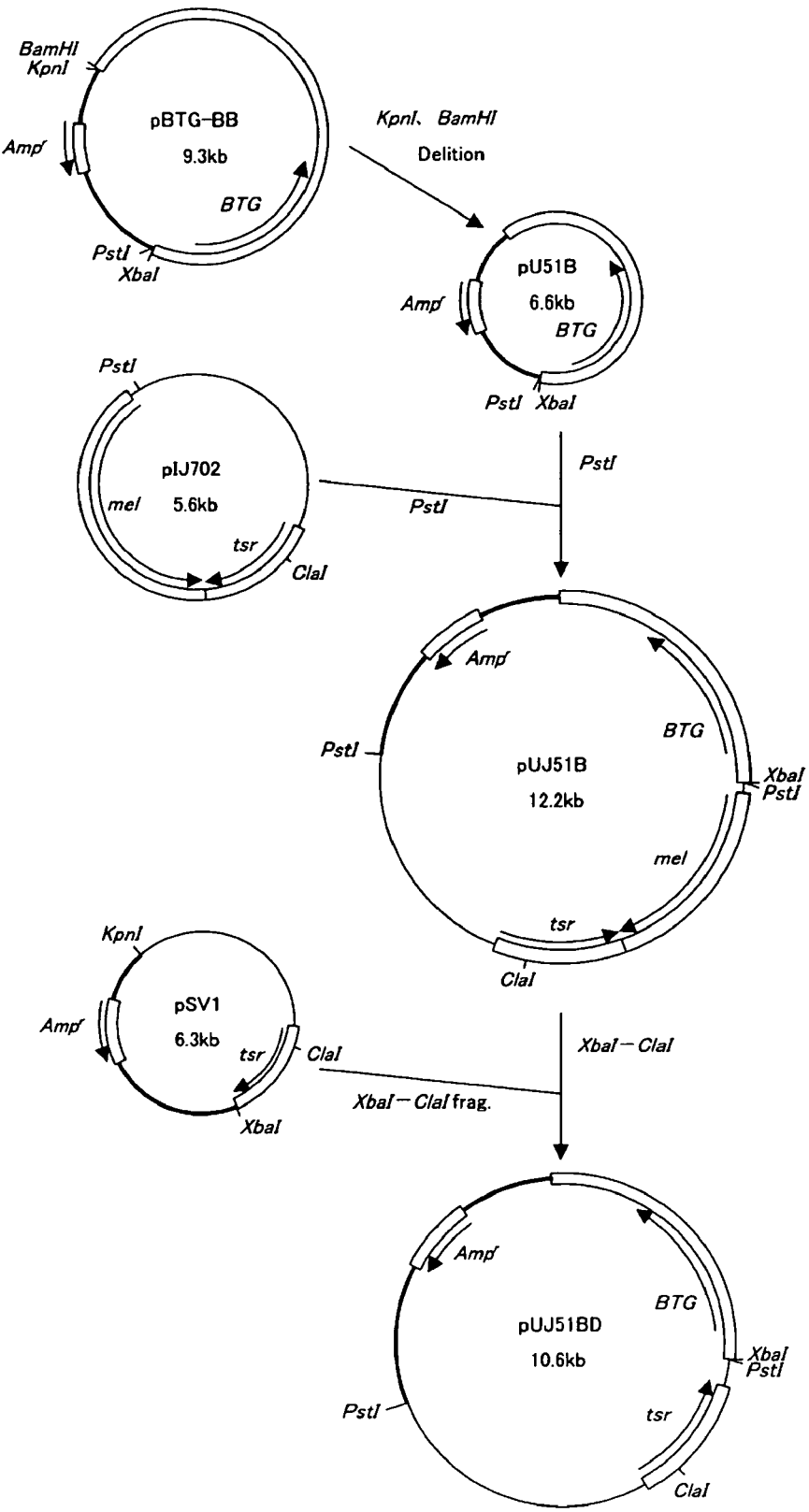
FIG. 2 shows a method of constructing a secretion expression plasmid pUJ51BD containing a transglutaminase gene.

A secretion expression plasmid pUJ51BD containing transglutaminase gene was constructed by the method shown in FIG. 2. First of all, a plasmid pBTG-BB was manufactured by cutting out about 6.6 kb of Bgl II-Bam HI fragment from a phage DNA (λBTG, Japanese Patent Unexamined Publication No. 5-199883) containing a transglutaminase (hereinafter, also referred to as "BTG") gene Bam HI fragment isolated from *Streptomyces mobaraensis* S-8112 (Accession number: FIRM P-18980) and by inserting the fragment into a Bam HI site of pUC19. A 3' unnecessary region was deleted from pBTG-BB by using Kilo-Sequence Deletion Kit (Takara Shuzo Co., Ltd.) to manufacture a plasmid pU51B containing about 3.9 kb of BTG gene. Then, a plasmid pUJ51B was manufactured by inserting Pst I-digested DNA fragment of actinomycetes vector pIJ702 into a Pst I site of pU51B. By cutting out a Xba I-Cla I fragment from pUJ51B and substituting it by a Xba I-Cla I fragment of *E. coli*-actinomycetes shuttle vector pSV1 obtained in Example 3, a BTG secretion expression plasmid pUJ51BD from which a mel (tyrosinase) gene derived from pIJ702 was removed was constructed.

Example 5

Analysis of Base Sequence of Promoter Region

A synthetic primer BB-23 [Invitrogen Corporation] 5'-ACACCGCACTCATAGTGGCG-3' (SEQ ID NO: 3) for analyzing a base sequence was synthesized from a sequence (SEQ ID NO: 1) of a structural gene of BTG. The base sequence of plasmid pBTG-BB was analyzed by using a primer BB-23 from 3' end of the promoter region and by using a M13-RV (Takara Shuzo Co., Ltd.) from 5' end of the promoter region. From the results of analysis of resultant base sequence, further synthesized primer BB-19 5'-TC-CGTGCGAGTGGAAGAACG-3' (SEQ ID NO: 4) and SP6-20 5'-GACGGCCTCCGAATAAC-3' (SEQ ID NO: 5) were synthesized. By the Primer walking method using these sequences, entire base sequence of about 700 bp of promoter region was determined (FIG. 3). Similarly, the base sequence of about 500 bp of terminator region was determined by the Primer walking method using synthetic primers SP6-32 5'-ATGTCGAGGGACAGGAAC-3' (SEQ ID NO: 6) and SP6-36 5'-CACCACGAAAGTCGCTAC-3' (SEQ ID NO: 7). As a result, a base sequence (SEQ ID NO: 2) consisting of a promoter region, a structural gene and a terminator region was identified (FIGS. 4 and 5). For Sequence reaction, BigDye™ Terminator Cycle Sequencing FS Ready Kit (Applied Biosystems) was used, and for analysis, ABI PRISM 310 Sequencer (Applied Biosystems) was used.

Example 6

Preparation of *Streptomyces lividans* 3131-TS Protoplast

*Streptomyces lividans* 3131-TS which had been obtained in Example 2 was cultured using a YEME medium (0.5% glycine) at 30° C. for two days. The 200 ml of cultured medium was centrifuged (1,300 g at room temperature for 10 minutes). The obtained cell body was suspended in 72 ml of 0.35 M saccharose solution. Then, this suspension was centrifuged (1,300 g at room temperature for 10 minutes) and the cell body was suspended again in 60 ml of buffer solution P containing 1 mg/ml of lysozyme (Sigma Aldrich Japan K.K.) and the suspension was incubated at 30° C. for 2.5 hours. The suspension after incubation was filtrated with absorbent cotton so as to remove residues. Then, the resultant filtrate was centrifuged (1,300 g at room temperature for 10 minutes) and the sediment was washed with 25 ml of buffer solution P. This washing was repeated twice and precipitation was suspended in 1 ml of buffer solution P to obtain a protoplast suspension.

| Buffer solution P | |
| --- | --- |
| TES [N-Tris(hydroxymethl)methyl-2-aminoethane sulphonic acid] | 5.73 g |
| Saccharose | 103 g |
| Mgnesium chloride | 2.03 g |
| Potassium sulfate | 0.5 g |
| Calcium chloride | 3.68 g |
| Trace element solution | 2 ml/L (pH 7.4) |

Note here that 1% monobasic potassium phosphate solution was prepared seperately, wich was added in the amount of 1 ml per 100 ml buffer solution P immediate before use.

| Trace element solution | |
| --- | --- |
| Zinc chloride | 40 mg |
| Ferric chloride | 200 mg |
| Cupric chloride | 10 mg |
| Manganese chloride | 10 mg |
| Sodium tetraborate | 10 mg |
| Ammonium molybdate | 10 mg/L |

Example 7

Transformation of *Streptomyces lividans* 3131-TS

| | |
| --- | --- |
| Each of the following solutions was mixed to the total amount | 140 μl. |
| DNA solution of BTG secretion expression plasmid pUJ51D | 20 μl |
| *Streptomyces lividans* 3131-TS protoplast | 100 μl |
| 0.35 M saccharose solution | 20 μl |

Then, 1.5 ml of buffer solution P containing 20% polyethylene glycol 1000 was added to the reaction mixture and mixed gently by pipetting. The resulting mixture was allowed to remain still for two minutes at room temperature. The mixture was centrifuged (1,700 g at room temperature for 10 minutes) to collect precipitate. Protoplast obtained as precipitate was washed twice with buffer solution P. The washed precipitate pellet was suspended in 1 ml of buffer solution P, and 200 μl each of the suspension was applied on an R-2 medium.

On the other hand, R-2/A and R-2/B as shown below were prepared.

| R-2/A | |
| --- | --- |
| Potassium Sulfate | 0.5 g |
| Magnesium Chloride | 20.2 g |
| Calcium Chloride | 5.9 g |
| Glucose | 20.0 g |
| Proline | 6.0 g |
| Casamino Acid | 0.2 g |
| Trace Element Solution | 4 ml |
| Agar | 44.0 g/L |
| R-2/B | |
| TES | 11.5 g |
| Yeast Extracts | 10.0 g |
| Sucrose | 203 g/L (pH 7.4) |

When a plate medium was produced, R-2/A and R-2/B were mixed and 1% $KH_2PO_4$ solution further was mixed in the amount of 1 ml per 200 ml final volume. The mixture was incubated at 30° C. for 18 hours. The surface of the plate medium was covered with 1 ml of buffer solution P consisting of 200 μg/ml of thiostrepton and 400 μg/ml of tyrosine. The resulting plates were further incubated at 30° C. for 7 days to obtain thiostrepton-resistant transformant (ABL-1).

Example 8

Preparation of Protoplast of *Streptomyces mobaraensis*

As preculture, *Streptomyces mobaraensis* S-8112 was cultured by using a YEME medium+1% glucose+25 mM magnesium chloride (pH 7.0) at 27° C. for three days. Then, the 0.5% precultured culture solution was inoculated on a YEME medium+1% glucose+4 mM magnesium chloride+glycine (pH 7.0) and cultured at 27° C. for three days. The cultured medium was centrifuged (3,000 g at 4° C. for 10 minutes) and the wet weight of the obtained cell body was measured. 0.6 g of wet cell body was washed with 10 ml of 0.3 M saccharose solution and centrifuged again (3,000 g at 4° C. for 10 minutes). The cell body was suspended in 4 ml of buffer solution BS-L consisting of 0.4 mg/ml of lysozyme (Roche Japan) and 0.1 mg/ml of Achromopeptidase (Wako Pure Chemical Industries, Ltd.) and gently stirred at 30° C. for 30 minutes. Then, 5 ml of buffer solution BS-P was added on ice and filtrated with absorbent cotton while washing with 3 ml of buffer solution BS-P so as to carry out filtration. The obtained suspension was centrifuged (1,500 g at 4° C. for 5 minutes), suspended in 10 ml of buffer solution BS-P, and then centrifuged again (1,500 g at 4° C. for 5 minutes). The obtained precipitate was suspended in 0.5 ml of buffer solution BS-P to obtain a protoplast suspension, which was used for the below mentioned transformation.

| Buffer solution BS-L | |
| --- | --- |
| 10% meat extracts | 10 ml |
| Yeast extracts | 1 g |
| Peptone | 2 g |

-continued

| | |
|---|---|
| Glucose | 10 g |
| Saccharose | 171.15 g |
| Calcium chloride | 0.277 g |
| Magnesium chloride | 0.508 g/L (pH 7.0) |
| Buffer solution BS-P | |
| 10% meat extracts | 10 ml |
| Yeast extracts | 1 g |
| Peptone | 2 g |
| Glucose | 10 g |
| Saccharose | 171.15 g |
| Calcium chloride | 2.77 g |
| Magnesium chloride | 2.03 g/L (pH 7.0) |

Example 9

Transformation of *Streptomyces mobaraensis*

After 100 μl of protoplast suspension (protoplast concentration: 1×10$^9$/ml) obtained in Example 8 and 10 μl of 2M saccharose solution containing 1 μg of BTG secretion expression plasmid pUJ51D obtained in Example 4 were mixed, immediately the mixture was allowed to remain still for 10 seconds. Then, after 0.5 ml of buffer solution P containing 25% polyethylene glycol 1000 (Sigma Aldrich Japan K.K.) was added to the mixture, the mixture was immediately allowed to remain still on ice for one minute. Then, after 2 ml of buffer solution BS-P was added to the mixture, the mixture was immediately centrifuged (1,500 g at 4° C. for 10 minutes). The resultant precipitate was suspended in 0.5 ml of buffer solution BS-P and 0.1 ml each of the suspension was dispended on a SBS agar medium to superpose it by using 3 ml of SBS agar medium while stirring. After removing the cover, the agar was dried for exactly two hours, and then cultured for exactly 24 hours at 27° C. Furthermore, 3 ml of SBS soft agar medium containing 200 μg/ml of thiostrepton was superposed and cultured at 27° C. The transformant obtained after the above-mentioned operation was defined as ABM-1.

| | |
|---|---|
| SBS agar medium (pH 7.0) | |
| Meat extracts | 10 g |
| Yeast extracts | 7.5 g |
| Tryptone peptone | 1 g |
| Glucose | 10 g |
| Saccharose | 308.07 g |
| Agar | 25 g/L (pH 7.0) |
| SBS soft agar medium (pH 7.0) | |
| Meat extracts | 10 g |
| Yeast extracts | 7.5 g |
| Tryptone peptone | 1 g |
| Glucose | 10 g |
| Saccharose | 308.07 g |
| Sea Plaque agarose | 25 g/L (pH 7.0) |

Example 10

Culture of Transformant in which BTG Gene was Incorporated

Transformant ABL-1 obtained in Example 7 and transformant ABM-1 obtained in Example 9 were cultured at 30° C. for 7 days under the following conditions, respectively.

| | |
|---|---|
| Poly peptone | 20 g |
| Soluble starch | 20 g |
| Yeast extracts | 2 g |
| Dipotassium phosphate | 2 g |
| Magnesium sulfate | 1 g |
| Adekanol LG126 | 0.5 g |
| 50 mg/mL thiostrepton solution | 0.5 ml/L (pH 7.0) |

The medium cultured under the above-mentioned conditions was centrifuged (12,000 g at 4° C. for 10 minutes) and the obtained supernatant was subjected to ELISA method.

Example 11

Measurement of Production Amount of BTG (ELISA Method)

From the culture supernatant of *Streptomyces mobaraensis* S-8112, the amount of BTG in the culture supernatant obtained in Example 10 was measured by the ELISA method using an anti-BTG antibody produced by immunizing a rabbit by using as an antigen purified BTG obtained in affinity chromatography using Blue Sepharose CL-6B (Pharmacia).

First of all, to each well of a 96-well micro plate, 100 μl each of anti-BTG antibody solution which had been diluted with PBS buffer was dispended, incubated at 37° C. for one hour, and immobilized on the plate. After removing the antibody solution, each well was washed with 200 μl of 10 times diluted solution of Block Ace (Dainippon Pharmaceutical Co., Ltd.) containing 0.1% Tween20 (hereinafter, referred to as "washing solution"). Washing was carried out successively three times. Then, 200 μl of 4 times diluted solution of Block Ace was dispended in each well and incubated at 37° C. for one hour so as to be blocked. After removing 4 times diluted solution of Block Ace, each well was washed with the washing solution three times. Then, measurement sample, i.e., culture supernatant (culture supernatant of ABL-1 or ABM-1) was appropriately diluted with 10 times diluted solution of Block Ace and 50 μl each of the diluted solution was dispended in each well and incubated at 37° C. for one hour. Note here that as standards, purified BTG which had been diluted with 10 times diluted solution of Block Ace were prepared at different concentrations. Similar to the measurement samples, the standards were also added to the well which had been subjected to blocking treatment.

After a sample solution was removed from each well, each well was washed with washing solution three times. Then, 100 μl of 10 times diluted solution of Block Ace containing Fab'-HRP obtained by cross-linking horseradish peroxidase (HRP) to Fab' fragment of anti-BTG antibody was dispended in each well and incubated at 37° C. for one hour. Then, after Fab'-HRP solution was removed, each well was washed with washing solution three times. Then, 150 μl each of 50 mM sodium citrate solution (pH 4.5) containing 0.04% orthophenylenediamine (o-PDA) and 0.42% peroxide solution was dispended in each well and incubated at 37° C. to allow o-PDA and peroxide to react with HRP for coloring. Exactly after 20 minutes from the start of the reaction, 50 μl each of 3M sulfuric acid solution as a stop solution of the reaction was dispended in each well, and the absorbance at 492 nm was measured. Then, by using a calibration curve calculated from the absorbance of standard, the amount of BTG in each culture supernatant (ABL-1 or ABM-1) was calculated. FIG. 6 is a table showing BTG amount per each culture supernatant. As shown in this table, BTG was produced in the amount of 0.7 g/L for ABL-1 and 0.5 g/L for ABM-1. When compared with the already reported productivity (40 mg/L to 50 mg/L), ten time or more of ABL-1 and about 10 times of AMB-1 were obtained. Thus, BTG productivity with extremely high efficiency was confirmed.

| Buffer solution PBS | |
|---|---|
| Sodium chloride | 8.0 g |
| Dipotassium phosphate | 1.1 g |
| Potassium chloride | 0.2 g |
| Monobasic potassium phosphate | 0.2 g/L (pH 7.4) |

Example 12

SDS-PAGE

Figure 7:
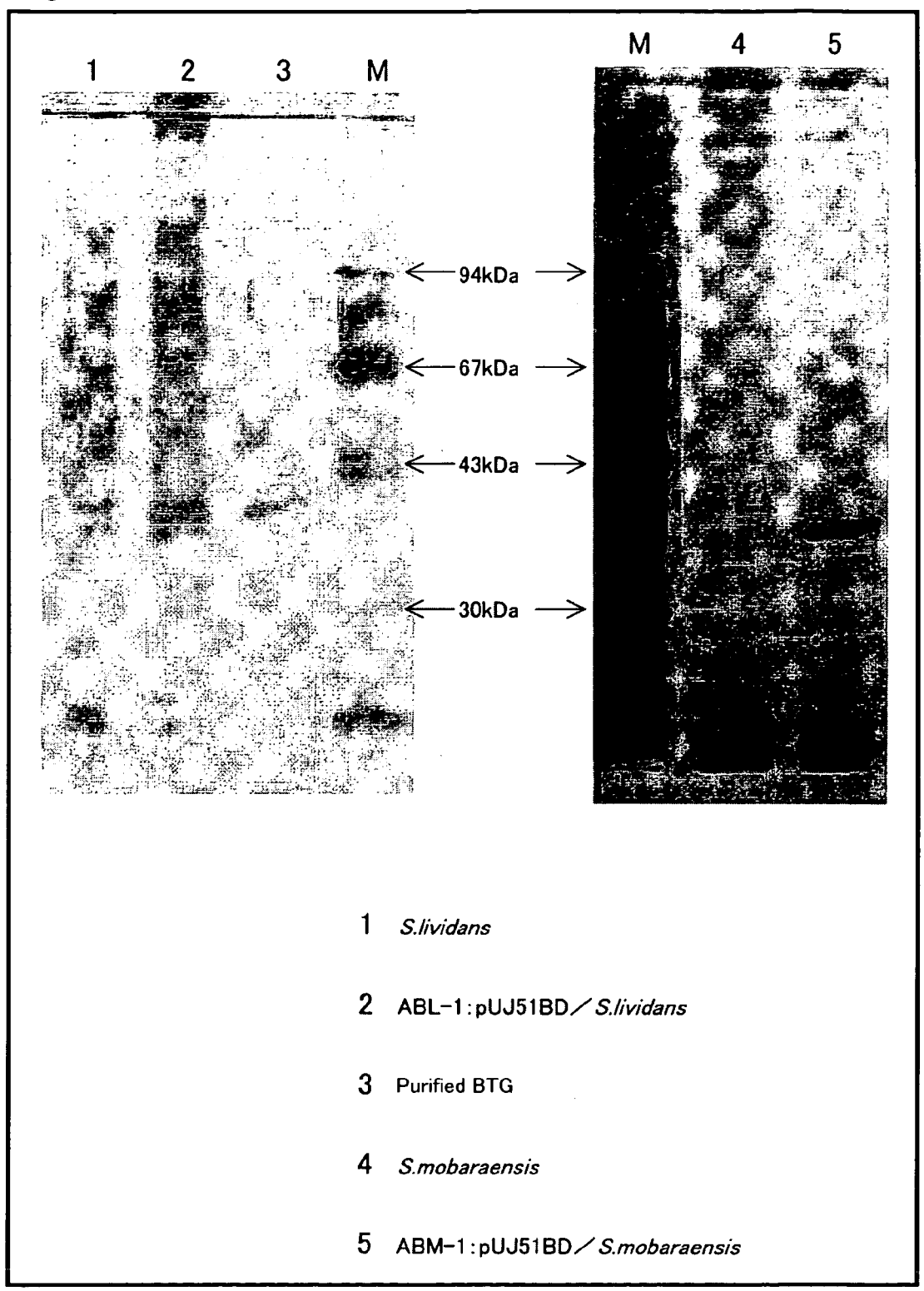
FIG. 7 shows the results of an electrophoresis of the culture supernatant of the transformants ABL-1 and ABM-1 (gel after silver staining). Lanes 1, 2, 3, 4 and 5 apply culture supernatant of *S. lividans* 3131-TS, culture supernatant of ABL-1, purified BTG, culture supernatant of *S. mobaraensis* S-8112, and culture supernatant of ABM-1, respectively. Lane M applies a molecular weight marker (Pharmacia).

The culture supernatants of transformant ABL-1 and transformant ABM-1 are mixed with 2× SDS buffer solution for electrophoresis at the ratio of 1:1, repeatedly and allowed them to be samples for SDS-PAGE. Note here that as the control, a culture supernatant of *Streptomyces lividans* 3131-TS, purified BTG diluted with a buffer solution, and a culture supernatant of *Streptomyces mobaraensis* S-8112 were prepared. Each sample was subjected to SDS-PAGE using 12.5% gel. For SDS-PAGE, Fast-System (Pharmacia Biotech) was used and for staining, silver staining was carried out. FIG. 7 shows photographs of gels after silver staining. In FIG. 7, lanes 1, 2, 3, 4 and 5 apply culture supernatant of *S. lividans* 3131-TS, culture supernatant of ABL-1, purified BTG, culture supernatant of *S. mobaraensis* S-8112, and culture supernatant of ABM-1, respectively. Lane M applies a molecular weight marker (Pharmacia).

As shown in FIG. 7, in ABL-1 (lane 2) and ABM-1 (lane 5), clear bands were observed in substantially the same positions in the purified BTG (lane 3), showing that BTG was contained at high concentration. On the other hand, in the culture supernatant of *Streptomyces lividans* (*S. lividans*) 3131-TS (lane 1) and the culture supernatant of *Streptomyces mobaraensis* (*S. mobaraensis*) S-8112 (lane 4), bands showing the purified BTG are not observed. This shows that in ABL-1 and ABM-1, BTG is specifically produced.

| Buffer solution 2xSDS | |
|---|---|
| Tris-HCl | 2.42 g |
| EDTA | 0.744 g |
| SDS | 50 g |
| β-mercaptoethanol | 100 ml/(pH 8.0) |

The present invention is not limited to the description of the above embodiments. A variety of modifications, which are within the scopes of the following claims and which are achieved easily by a person skilled in the art, are included in the present invention.

Hereinafter, the following matters are disclosed.

(1) A process for producing transglutaminase, comprising the steps of:

transforming a host *Streptomyces mobaraensis* by using a vector containing a structural gene of transglutaminase derived from *Streptomyces mobaraensis*, and a promoter and a terminator acting on the structural gene;

culturing the transformant under the conditions where the structural gene can be expressed; and collecting the produced transglutaminase.

(2) The process for producing transglutaminase described in (1), wherein the step of transforming is carried out under the conditions where the host *Streptomyces mobaraensis* can be grown.

(3) The process for producing transglutaminase described in (1) or (2), wherein the vector comprises a plasmid obtained by modifying a plasmid pIJ702.

(4) The process for producing transglutaminase described in any of (1) to (3), wherein the promoter is a promoter of transglutaminase derived from *Streptomyces mobaraensis*.

(5) The process for producing transglutaminase described in any of (1) to (4), wherein the terminator is a terminator of transglutaminase derived from *Streptomyces mobaraensis*.

(6) The process for producing transglutaminase described in any of (1) to (5), wherein the host *Streptomyces mobaraensis* is *Streptomyces mobaraensis* S-8112 or a mutant strain thereof.

(7) The process for producing transglutaminase described in any of (1) to (6), wherein the structural gene comprises a sequence set forth in SEQ ID NO: 1 or a sequence obtained by modifying a part of the sequence, the sequence encoding transglutaminase.

(8) The process for producing transglutaminase described in any of (1) to (6), wherein the transformant comprises a DNA fragment having an externally introduced sequence set forth in SEQ ID NO: 2 or sequence obtained by modifying a part of the sequence, the sequence encoding transglutaminase.

(11) A process for producing transglutaminase, comprising the steps of:

transforming a host *Streptomyces lividans* by using a vector containing a structural gene of transglutaminase derived from *Streptomyces mobaraensis*, and a promoter and a terminator acting on the structural gene;

culturing the transformant under the conditions where the structural gene can be expressed; and collecting the produced transglutaminase.

(12) The process for producing transglutaminase described in (11), wherein the step of transforming is carried out under the conditions where the host *Streptomyces lividans* can be grown.

(13) The process for producing transglutaminase described in (11) or (12), wherein the vector comprises a plasmid obtained by modifying a plasmid pIJ702.

(14) The process for producing transglutaminase described in any of (11) to (13), wherein the promoter is a promoter of transglutaminase derived from *Streptomyces mobaraensis*.

(15) The process for producing transglutaminase described in any of (11) to (14), wherein the terminator is a terminator of transglutaminase derived from *Streptomyces mobaraensis*.

(16) The process for producing transglutaminase described in any of (11) to (15), wherein the host *Streptomyces lividans* is *Streptomyces lividans* 3131 or a mutant strain thereof.

(17) The process for producing transglutaminase described in any of (11) to (16), wherein the structural gene comprises a sequence set forth in SEQ ID NO: 1 or a sequence obtained by modifying a part of the sequence, the sequence encoding transglutaminase.

(18) The process for producing transglutaminase described in any of (11) to (16), wherein the transformant comprises a DNA fragment having an externally introduced sequence set forth in SEQ ID NO: 2 or sequence obtained by modifying a part of the sequence, the sequence encoding transglutaminase.

(21) An expression vector comprising a structural gene of transglutaminase derived from *Streptomyces mobaraensis*, and a promoter and a terminator acting on the structural gene.

(22) The expression vector described in any of (21), wherein the promoter is a promoter of transglutaminase derived from *Streptomyces mobaraensis*.

(23) The expression vector described in any of (21) or (22), wherein the terminator is a terminator of transglutaminase derived from *Streptomyces mobaraensis*.

(24) The expression vector described in any of (21) to (23), wherein the structural gene comprises a sequence set forth in SEQ ID NO: 1 or a sequence obtained by modifying a part of the sequence, the sequence encoding transglutaminase.

(25) An expression vector having a sequence comprising a sequence set forth in SEQ ID NO: 2 or a sequence obtained by modifying a part of the sequence, the sequence encoding transglutaminase.

(26) A micro-organism belonging to *Streptomyces*, which was transformed by using any of expression vectors of (21) to (25).

(31) A process for transforming actinomycetes, comprising the steps of:

allowing a host actinomycetes to be a protoplast under the conditions where it can be grown; and introducing an expression vector comprising a structural gene of transglutaminase derived from *Streptomyces mobaraensis*, and a promoter and a terminator acting on the structural gene; into host actinomycetes under the conditions where the host actinomycetes can be grown.

(32) The process for transforming actinomycetes described in (31), the host actinomycetes is either *Streptomyces mobaraensis* or *Streptomyces lividans*.

INDUSTRIAL APPLICABILITY

The present invention provides an actinomycetes capable of producing transglutaminase with extremely high productivity. The use of the actinomycetes makes it possible to produce transglutaminase at a high efficiency.

The invention claimed is:

1. A transformant of *Streptomyces mobaraensis*, comprising a gene encoding transglutaminase isolated from *Streptomyces mobaraensis* and a promoter promoting transcription of the gene and a terminator serving to terminate transcription of the gene,
   wherein the gene comprises the sequence set forth in SEQ ID NO: 1;
   and wherein the terminator is a terminator of transglutaminase isolated from *Streptomyces mobaraensis*.

2. The transformant of *Streptomyces mobaraensis* according to claim 1, wherein the promoter is a promoter of transglutaminase isolated from *Streptomyces mobaraensis*.

3. A transformant of *Streptomyces mobaraensis* comprising a DNA fragment having an externally introduced sequence set forth in SEQ ID NO: 2.

4. The transformant of *Streptomyces mobaraensis* according to claim 1, which is a transformant of *Streptomyces mobaraensis* S-8112.

5. A process for producing transglutaminase, comprising the steps of:
   culturing a transformant of *Streptomyces mobaraensis* comprising a gene encoding transglutaminase isolated from *Streptomyces mobaraensis* and a promoter promoting the transcription of the gene and a terminator serving to terminate transcription of the gene, under the conditions where the gene can be expressed; and
   collecting the produced transglutaminase,
   wherein the gene comprises the sequence set forth in SEQ ID NO: 1;
   and wherein the terminator is a terminator of transglutaminase isolated from *Streptomyces mobaraensis*.

6. The process for producing transglutaminase according to claim 5, wherein the promoter is a promoter of transglutaminase isolated from *Streptomyces mobaraensis*.

7. The process for producing transglutaminase, comprising the steps of:
   culturing a transformant of *Streptomyces mobaraensis* comprising a gene encoding transglutaminase isolated from *Streptomyces mobaraensis* and a promoter promoting the transcription of the gene and a terminator serving to terminate transcription of the gene, under the conditions where the gene can be expressed; and
   collecting the produced transglutaminase,
   wherein the transformant of *Streptomyces mobaraensis* comprises a DNA fragment having an externally introduced sequence set forth in SEQ ID NO: 2;
   and wherein the terminator is a terminator of transglutaminase isolated from *Streptomyces mobaraensis*.

8. The process for producing transglutaminase according to claim 5, wherein the transformant of *Streptomyces mobaraensis* is a transformant of *Streptomyces mobaraensis* S-8112.

9. A transformant of *Streptomyces lividans* comprising a gene encoding transglutaminase isolated from *Streptomyces mobaraensis*, and a promoter promoting the transcription of the gene and a terminator serving to terminate transcription of the gene, wherein the gene comprises the sequence set forth in SEQ ID NO: 1;
   and wherein the terminator is a terminator of transglutaminase isolated from *Streptomyces mobaraensis*.

10. The transformant of *Streptomyces lividans* according to claim 9, wherein the promoter is a promoter of transglutaminase isolated from *Streptomyces mobaraensis*.

11. A transformant of *Streptomyces lividans* comprising a DNA fragment having an externally introduced sequence set forth in SEQ ID NO: 2.

12. The transformant of *Streptomyces lividans* according to claim 9, which is a transformant of *Streptomyces lividans* 3131.

13. A process for producing transglutaminase, comprising the steps of:
   culturing a transformant of *Streptomyces lividans* comprising a gene encoding transglutaminase isolated from *Streptomyces mobaraensis*, and a promoter promoting the transcription of the gene and a terminator serving to terminate transcription of the gene, under the conditions where the gene can be expressed; and
   collecting the produced transglutaminase, wherein the gene comprises the sequence set forth in SEQ ID NO: 1;
   and wherein the terminator is a terminator of transglutaminase isolated from *Streptomyces mobaraensis*.

14. The process for producing transglutaminase according to claim 13, wherein the promoter is a promoter of transglutaminase isolated from *Streptomyces mobaraensis*.

15. The process for producing transglutaminase comprising the steps of:
   culturing a transformant of *Streptomyces lividans* comprising a gene encoding transglutaminase isolated from *Streptomyces mobaraensis*, and a promoter promoting the transcription of the gene and a terminator serving to terminate transcription of the gene, under the conditions where the gene can be expressed; and
   collecting the produced transglutaminase,
   wherein the transformant of *Streptomyces lividans* comprises a DNA fragment having an externally introduced sequence set forth in SEQ ID NO: 2;
   and wherein the terminator is a terminator of transglutaminase isolated from *Streptomyces mobaraensis*.

16. The process for producing transglutaminase according to claim 13, wherein the transformant of *Streptomyces lividans* is a transformant of *Streptomyces lividans* 3131.

17. A transformant of *Streptomyces mobaraensis* comprising a gene encoding transglutaminase and a promoter promoting the transcription of the gene and a terminator serving to terminate transcription of the gene,
   wherein the gene comprises a sequence obtained by modifying SEQ ID NO: 1, such that the modified sequence hybridizes to DNA of SEQ ID NO: 1 under conditions of 50% formamide, 10×SSC, 5× Denhardt solution, 1% SDS, 10% dextran sulfate, 10 µg/ml denatured salmon sperm DNA and 50 mM phosphoric acid buffer (pH 7.5) at 42° C., followed by washing with 0.1×SSC and 0.1% SDS at 68° C., and the modified sequence encodes a protein having transglutaminase activity;

and wherein the terminator is a terminator of transglutaminase isolated from *Streptomyces mobaraensis*.

18. A transformant of *Streptomyces mobaraensis* comprising a gene encoding transglutaminase and a promoter promoting the transcription of the gene and a terminator serving to terminate transcription of the gene, which are externally introduced, wherein the gene and the promoter and the terminator comprise a sequence obtained by modifying SEQ ID NO: 2, such that the modified sequence hybridizes to DNA of SEQ ID NO: 2 under conditions of 50% formamide, 10×SSC, 5× Denhardt solution, 1% SDS, 10% dextran sulfate, 10 μg/ml denatured salmon sperm DNA and 50 mM phosphoric acid buffer (pH 7.5) at 42° C., followed by washing with 0.1×SSC and 0.1% SDS at 68° C., and the modified sequence encodes a protein having transglutaminase activity;

and wherein the terminator is a terminator of transglutaminase isolated from *Streptomyces mobaraensis*.

19. The transformant of *Streptomyces mobaraensis* according to claim 1, which is a transformant of a strain obtained by mutating *Streptomyces mobaraensis* S-8112.

20. A process for producing transglutaminase, comprising the steps of:

culturing a transformant of *Streptomyces mobaraensis* comprising a gene encoding transglutaminase and a promoter promoting the transcription of the gene and a terminator serving to terminate transcription of the gene, under the conditions where the gene can be expressed; and collecting the produced transglutaminase;

wherein the gene comprises a sequence obtained by modifying SEQ ID NO: 1, such that the modified sequence hybridizes to DNA of SEQ ID NO: 1 under conditions of 50% formamide, 10×SSC, 5× Denhardt solution, 1% SDS, 10% dextran sulfate, 10 μg/ml denatured salmon sperm DNA and 50 mM phosphoric acid buffer (pH 7.5) at 42° C., followed by washing with 0.1×SSC and 0.1% SDS at 68° C., and the modified sequence encodes a protein having transglutaminase activity;

and wherein the terminator is a terminator of transglutaminase isolated from *Streptomyces mobaraensis*.

21. A process for producing transglutaminase, comprising the steps of:

culturing a transformant of *Streptomyces mobaraensis* comprising a gene encoding transglutaminase and a promoter promoting the transcription of the gene and a terminator serving to terminate transcription of the gene, under the conditions where the gene can be expressed; and collecting the produced transglutaminase;

wherein the gene and the promoter and the terminator gene comprise a sequence obtained by modifying SEQ ID NO: 2, such that the modified sequence hybridizes to DNA of SEQ ID NO: 2 under conditions of 50% formamide, 10×SSC, 5× Denhardt solution, 1% SDS, 10% dextran sulfate, 10 μg/ml denatured salmon sperm DNA and 50 mM phosphoric acid buffer (pH 7.5) at 42° C., followed by washing with 0.1×SSC and 0.1% SDS at 68° C., and the modified sequence encodes a protein having transglutaminase activity;

and wherein the terminator is a terminator of transglutaminase isolated from *Streptomyces mobaraensis*.

22. The process for producing transglutaminase according to claim 5, wherein the transformant of *Streptomyces mobaraensis* is a transformant of a strain obtained by mutating *Streptomyces mobaraensis* S-8112.

23. A transformant of *Streptomyces lividans* comprising a gene encoding transglutaminase and a promoter promoting the transcription of the gene and a terminator serving to terminate transcription of the gene, wherein the gene comprises a sequence obtained by modifying SEQ ID NO: 1, such that the modified sequence hybridizes to DNA of SEQ ID NO: 1 under conditions of 50% formamide, 10×SSC, 5× Denhardt solution, 1% SDS, 10% dextran sulfate, 10 μg/ml denatured salmon sperm DNA and 50 mM phosphoric acid buffer (pH 7.5) at 42° C., followed by washing with 0.1×SSC and 0.1% SDS at 68° C., and the modified sequence encodes a protein having transglutaminase activity;

and wherein the terminator is a terminator of transglutaminase isolated from *Streptomyces mobaraensis*.

24. A transformant of *Streptomyces lividans* comprising a gene encoding transglutaminase and a promoter promoting on the transcription of the gene and a terminator serving to terminate transcription of the gene, wherein the gene and the promoter and the terminator comprise a sequence obtained by modifying SEQ ID NO: 2, such that the modified sequence hybridizes to DNA of SEQ ID NO: 2 under conditions of 50% formamide, 10×SSC, 5× Denhardt solution, 1% SDS, 10% dextran sulfate, 10 μg/ml denatured salmon sperm DNA and 50 mM phosphoric acid buffer (pH 7.5) at 42° C., followed by washing with 0.1×SSC and 0.1% SDS at 68° C., and the modified sequence encodes a protein having transglutaminase activity;

and wherein the terminator is a terminator of transglutaminase isolated from *Streptomyces mobaraensis*.

25. The transformant of *Streptomyces lividans* according to claim 9, which is a transformant of a strain obtained by mutating *Streptomyces lividans* 3131.

26. A process for producing transglutaminase, comprising the steps of:

culturing a transformant of *Streptomyces lividans* comprising a gene encoding transglutaminase and a promoter promoting the transcription of the gene and a terminator serving to terminate transcription of the gene, under the conditions where the gene can be expressed; and collecting the produced transglutaminase;

wherein the gene comprises a sequence obtained by modifying SEQ ID NO: 1, such that the modified sequence hybridizes to DNA of SEQ ID NO: 1 under conditions of 50% formamide, 10×SSC, 5× Denhardt solution, 1% SDS, 10% dextran sulfate, 10 μg/ml denatured salmon sperm DNA and 50 mM phosphoric acid buffer (pH 7.5) at 42° C., followed by washing with 0.1×SSC and 0.1% SDS at 68° C., and the modified sequence encodes a protein having transglutaminase activity;

and wherein the terminator is a terminator of transglutaminase isolated from *Streptomyces mobaraensis*.

27. A process for producing transglutaminase, comprising the steps of:

culturing a transformant of *Streptomyces lividans* comprising a gene encoding transglutaminase and a promoter promoting the transcription of the gene and a terminator serving to terminate transcription of the gene, under the conditions where the gene can be expressed; and collecting the produced transglutaminase;

wherein the gene and the promoter and the terminator comprise a sequence obtained by modifying SEQ ID NO: 2, such that the modified sequence hybridizes to DNA of SEQ ID NO: 2 under conditions of 50% formamide, 10×SSC, 5× Denhardt solution, 1% SDS, 10% dextran sulfate, 10 μg/ml denatured salmon sperm DNA and 50 mM phosphoric acid buffer (pH 7.5) at 42° C., followed by washing with 0.1×SSC and 0.1% SDS at 68° C., and the modified sequence encodes a protein having transglutaminase activity;

and wherein the terminator is a terminator of transglutaminase isolated from *Streptomyces mobaraensis*.

28. The process for producing transglutaminase according to claim 13, wherein the transformant of *Streptomyces lividans* is a transformant of a strain obtained by mutating *Streptomyces lividans* 3131.

* * * * *